United States Patent
Halderman et al.

(10) Patent No.: US 11,690,495 B2
(45) Date of Patent: Jul. 4, 2023

(54) SYSTEMS AND METHODS FOR HIGH-SPEED DATA TRANSMISSION ACROSS AN ELECTRICAL ISOLATION BARRIER

(71) Applicant: Intuitive Surgical Operations, Inc., Sunnyvale, CA (US)

(72) Inventors: Jonathan D. Halderman, Sunnyvale, CA (US); John A Barton, Mountain View, CA (US); Marc Levesque, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 285 days.

(21) Appl. No.: 17/052,119

(22) PCT Filed: Jun. 5, 2019

(86) PCT No.: PCT/US2019/035679
§ 371 (c)(1),
(2) Date: Oct. 30, 2020

(87) PCT Pub. No.: WO2019/236774
PCT Pub. Date: Dec. 12, 2019

(65) Prior Publication Data
US 2021/0113062 A1    Apr. 22, 2021

Related U.S. Application Data

(60) Provisional application No. 62/681,594, filed on Jun. 6, 2018.

(51) Int. Cl.
*A61B 1/00* (2006.01)
*A61B 1/04* (2006.01)
(Continued)

(52) U.S. Cl.
CPC ...... *A61B 1/00013* (2013.01); *A61B 1/00018* (2013.01); *A61B 1/042* (2013.01);
(Continued)

(58) Field of Classification Search
CPC ..... H04B 10/80; H04B 10/801; H04B 10/802
(Continued)

(56) References Cited

U.S. PATENT DOCUMENTS 4,024,501 A * 5/1977 Herring ................... H04L 25/26
375/220
5,671,738 A 9/1997 Thornberg
(Continued)

OTHER PUBLICATIONS

International Preliminary Report on Patentability for Application No. PCT/2019/035679, dated Dec. 17, 2020, 9 pages.
(Continued)

*Primary Examiner* — Aaron B Fairchild

(57) ABSTRACT

An exemplary medical system includes a first electrical circuit (204-1) on a PCB (206), a second electrical circuit (204-2) on the PCB and electrically isolated from the first electrical circuit, and a free space optics interface assembly (302) on the PCB. The free space optics assembly includes a housing (402) defining a free space chamber (404) in the housing, an optical transmitter (416) having an input (426) that is electrically coupled to the first electrical circuit, and an optical receiver (418) in optical communication with the optical transmitter via the free space chamber and having an output (432) that is electrically coupled to the second electrical circuit. The optical transmitter and the optical receiver are hermetically sealed within the housing.

19 Claims, 8 Drawing Sheets

(51) Int. Cl.
  *H04B 10/50*  (2013.01)
  *H04B 10/60*  (2013.01)
  *A61B 1/07*  (2006.01)

(52) U.S. Cl.
  CPC ............ *H04B 10/50* (2013.01); *H04B 10/60* (2013.01); *A61B 1/07* (2013.01)

(58) Field of Classification Search
  USPC .......................................................... 250/551
  See application file for complete search history.

(56) References Cited

U.S. PATENT DOCUMENTS

| | | | |
|---|---|---|---|
| 6,870,176 B2* | 3/2005 | Rohrbacher | .......... H01L 31/162 257/E31.015 |
| 2001/0048254 A1* | 12/2001 | Engel | ..................... H02K 29/08 310/68 B |
| 2008/0187013 A1 | 8/2008 | Guenter et al. | |
| 2013/0313447 A1* | 11/2013 | Tay | ..................... H01L 31/0203 250/551 |
| 2014/0276768 A1 | 9/2014 | Juergens et al. | |
| 2018/0035873 A1 | 2/2018 | Kohler et al. | |

OTHER PUBLICATIONS

International search report and written opinion for application No. PCT/US2019/035679 dated Sep. 26, 2019, 16 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR HIGH-SPEED DATA TRANSMISSION ACROSS AN ELECTRICAL ISOLATION BARRIER

RELATED APPLICATIONS

The present application claims priority to U.S. Provisional Patent Application No. 62/681,594, filed on Jun. 6, 2018, and entitled "SYSTEMS AND METHODS FOR HIGH-SPEED DATA TRANSMISSION ACROSS AN ELECTRICAL ISOLATION BARRIER," the contents of which are hereby incorporated by reference in their entirety.

BACKGROUND INFORMATION

Electrosurgical energy is a safe and effective tool used during surgery. During an electrosurgical procedure, such as a minimally invasive surgical procedure that uses a computer-assisted surgical system, an electrosurgical unit located within an operating room generates and outputs high voltage, high frequency electrical current. The electrical current is applied to patient tissue by way of an active electrode to cauterize or otherwise manipulate the tissue. To safely return the electrical current from the patient back to the electrosurgical unit, a grounding pad is adhered to the patient's skin. Because the conductive surface area of the grounding pad is much larger than the active electrode, the electrical current is dispersed over a wide area, minimizing the heating of the tissue under the grounding pad and thereby preventing inadvertent patient burn.

To assist the surgeon during a typical electrosurgical procedure, an endoscope is used to provide images (e.g., stereoscopic video) of a surgical area that includes the tissue being cauterized. An exemplary endoscope includes a metal shaft that extends distally from a camera head into the patient. Circuitry at the distal end of the shaft captures images (either monoscopic or stereoscopic) using image sensors and transmits the images to circuitry in the camera head. The circuitry processes the images (e.g., by performing various control and data transmission functions on the images) and transmits data (e.g., video data) representative of the images to a display system located within the operating room by way of an electrical cable.

In some situations, the electrical cable inadvertently comes in contact with the floor of the operating room, a metal tray, or another grounded surface. In these situations, the electrical cable acts as a capacitor due to the gap that an outer insulative jacket of the electrical cable creates between wires included in the electrical cable and the ground surface. Because the electrical current applied by the active electrode is high frequency, the electrical current can pass through the capacitor formed by the electrical cable with relative ease. Hence, while the electrical cable is in contact with the grounded surface, a path to ground for the electrical current is created. For example, if the any portion of the metal shaft of the endoscope comes in contact with or in close proximity to patient tissue to which high frequency electrical current is being applied, the high frequency electrical current may, instead of being dissipated by the grounding pad, be capacitively coupled onto the metal shaft and travel through the circuitry included in the camera head to the grounded surface that the electrical cable is touching. As the high frequency electrical current is capacitively coupled onto the metal shaft, an electric discharge (e.g., an electric arc) may occur between the patient tissue and the metal shaft. Often, such a discharge causes no harm to the patient. But, capacitively coupled current creates a potential situation in which a discharge may injure (e.g., burn) a patient.

To prevent capacitive coupling of electrical current onto the metal shaft of the endoscope, the circuitry within the endoscope may include an isolation barrier that electrically isolates circuit components electrically and/or capacitively coupled to the shaft (or to components within the shaft) from circuit components connected to the wires included in the electrical cable. In this manner, an electrically conductive path between the metal shaft and the electrical cable is blocked.

While the isolation barrier may prevent capacitive coupling of electrical current onto the metal shaft of the endoscope, the isolation barrier disadvantageously presents a challenge for transmitting data between electrically isolated components, especially between electrically isolated components on a relatively small printed circuit board ("PCB") such as that used in a camera head of an endoscope. Conventional solutions for transmitting data across an isolation barrier implemented on similarly sized PCBs are limited in bandwidth and can only transmit data at relatively low data transmission rates (e.g., less than 1 gigabit per second ("Gbps")). But, these low data transmission rates may cause latency, poor image quality, and/or inefficiency in scenarios in which endoscopic images are presented to a surgeon in substantially real time, especially when the endoscopic images are data intensive (e.g., such as is the case with high-definition stereoscopic images).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
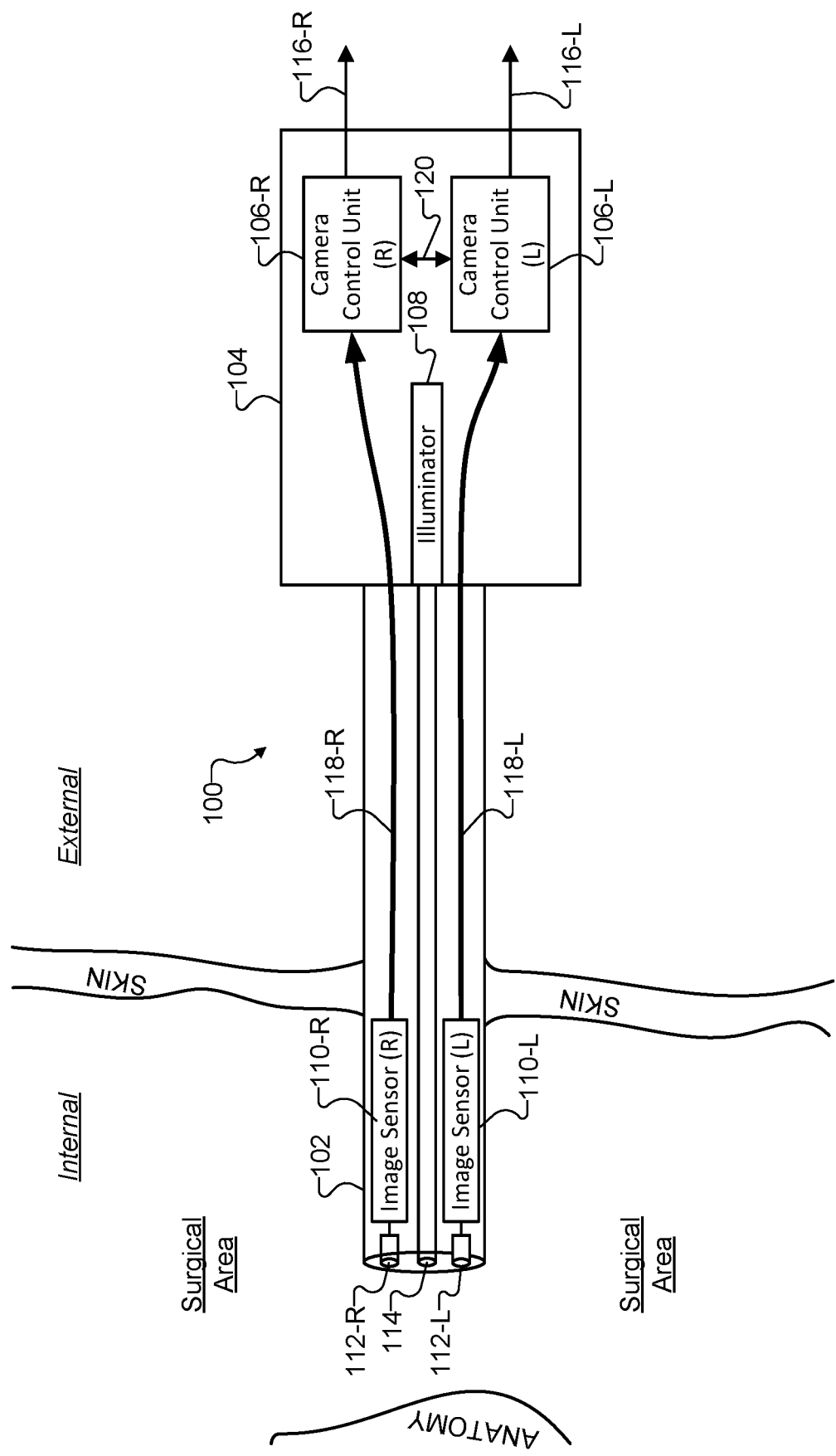
FIG. 1 illustrates an exemplary stereoscopic endoscope according to principles described herein.

Systems and methods for high-speed data transmission across an electrical isolation barrier are described herein. As will be described in more detail below, an exemplary medical system includes a first electrical circuit, a second electrical circuit electrically isolated from the first electrical circuit, and a free space optics interface assembly all on a single PCB. The free space optics interface assembly is configured to allow high-speed transmission (greater than 1 Gbps) of data between the first and second electrical circuits. To this end, the free space optics interface assembly includes a housing defining a free space chamber in the housing, an optical transmitter having an input that is electrically coupled to the first electrical circuit, and an optical receiver in optical communication with the optical transmitter via the free space chamber and having an output that is electrically coupled to the second electrical circuit. In this configuration, the optical transmitter transmits, into the free space chamber, modulated light representative of data provided by the first electrical circuit. The optical receiver receives the modulated light. A demodulator component included in the second electrical circuit demodulates the light back into the data. The demodulated or otherwise processed data is presented at an output of the second electrical circuit. In some examples, the second electrical circuit transmits the data to a computing device located off the PCB.

In some examples, the PCB is included in a surgical instrument configured to be used in a surgical procedure (e.g., a minimally invasive surgical procedure performed by a computer-assisted surgical system). To illustrate, the PCB may be housed within a camera head of an endoscope. In this illustration, a shaft (e.g., a conductive metal shaft) that includes one or more image sensors extends from the camera head. At the distal end of the shaft are one or more lenses or other optics configured to capture light reflecting from internal patient anatomy when positioned within a surgical area. The one or more image sensors convert the light to signals (e.g., digital data) representative of images and transmit the signals to the camera head by way of one or more conduits within the shaft. The first electrical circuit on the PCB processes the signals and generates data based on the signals. The data is representative of or is otherwise associated with one or more images of the surgical area. The first electrical circuit transmits the data across an electrical isolation barrier to the second electrical circuit by way of the free space optics interface assembly in any of the ways described herein. The second electrical circuit further processes the data and/or transmits the data via an electrical cable to a computing device located off of the PCB. For example, the second electrical circuit may transmit the data by way of the electrical cable to a computerized image processing device that is a part of a display system. The display system uses the data to display the one or more images.

Various benefits may be provided by the systems and methods described herein. For example, the systems and methods described herein allow high-speed transmission of data across an electrical isolation barrier implemented on a relatively small PCB, such as a PCB in a surgical instrument. In such configurations, the interface assembly used to allow the transmission of data across an electrical isolation barrier must be relatively small (e.g., implemented in a package that is approximately 30 mm by 16 mm by 8 mm). Conventional interface assemblies of this size (e.g., optoisolators) can only transmit data at relatively low data transmission rates (e.g., less than 1 Gbps). Other conventional interface assemblies (e.g., interface assemblies that include optical fibers and transceivers) are too large to fit on PCBs in many surgical instruments. In contrast, the free space optics interface assemblies described herein may be implemented in relatively small packages (e.g., a package that is approximately 30 mm by 16 mm by 8 mm or of any other suitable size that allows the free space optics interface assemblies to be included on a PCB that is housed within a surgical instrument) while still allowing data transmission rates of greater than 1 Gbps (e.g., 4 Gbps or any other suitable data transmission rate greater than 1 Gbps). By allowing such high data transmission rates across an electrical isolation barrier, the systems and methods described herein enable efficient and real-time processing of data intensive content, such as high-definition stereoscopic images generated by a stereoscopic endoscope.

Furthermore, the free space optics interface assemblies described herein are suitable for use in surgical settings, such as in an operating room. For example, the free space optics interface assemblies described herein are hermetically sealed and configured to withstand any suitable operating room sterilization process (e.g., an autoclave process, an ultrasonic cleaning, an alkaline chemical soak, etc.).

The systems and methods described herein reduce or eliminate the risk of electric discharge caused by capacitively coupled current onto a surgical instrument positioned within a surgical area. For example, by electrically isolating electrical circuits on a PCB located within a surgical instrument, and by using a free space optics interface assembly as described herein to transmit data between the electrical circuits, the systems and methods described herein prevent electrical current (e.g., high frequency current applied by an electrosurgical tool to patient tissue) from being capacitively coupled onto the surgical instrument and thereby creating an electric discharge that could potentially burn or otherwise harm the patient. This is especially the case when a surgical team inserts the surgical instrument into the patient through a non-electrically conductive (e.g., plastic) cannula instead of through an electrically conductive (e.g., metal) cannula that is, for example, connected to an electrical grounding pad.

The systems and methods described herein may operate as part of or in conjunction with manually controlled surgical instruments. For example, the systems and methods described herein may operate within a manually controlled endoscope.

Additionally or alternatively, the systems and methods described herein may operate as part of or in conjunction with a computer-assisted surgical system. A computer-assisted surgical system may use robotic and/or teleoperation technology to perform a surgical procedure on a patient. Exemplary computer-assisted surgical systems are described in U.S. Pat. No. 5,299,288 (filed Sep. 18, 1991)(disclosing "Image-directed robotic system for precise robotic surgery including redundant consistency checking"); U.S. Pat. No. 5,397,323 (filed Oct. 30, 1992)(disclosing "Remote Center-of-motion Robot for Surgery"); U.S. Pat. No. 5,402,801 (filed Apr. 28, 1994)(disclosing "System and Method for Augmentation of Surgery"); U.S. Pat. No. 5,417,210 (filed May 27, 1992)(disclosing "System and method for augmentation of endoscopic surgery"); U.S. Pat. No. 5,445,166 (filed Apr. 6, 1994)(disclosing "System for Advising a Surgeon"); U.S. Pat. No. 5,631,973 (filed May 5, 1994) (disclosing "Method for telemanipulation with telepresence"); U.S. Pat. No. 5,649,956 (filed Jun. 7, 1995)(disclosing "System and method for releasably holding a surgical instrument"); U.S. Pat. No. 5,696,837 (filed Apr. 20, 1995) (disclosing "Method and apparatus for transforming coordinate systems in a telemanipulation system"); U.S. Pat. No. 5,931,832 (filed Jul. 20, 1995)(disclosing "Methods for positioning a surgical instrument about a remote spherical center of rotation"); and U.S. Pat. No. 6,999,852 B1 (filed Oct. 26, 2004)(disclosing "Flexible robotic surgery system and method")—all incorporated herein by reference in their entirety. In addition, persons of skill in the art will be familiar with computer-assisted surgical systems such as the da Vinci Xi® Surgical System (Model IS4000) commercialized by Intuitive Surgical, Inc., Sunnyvale, Calif.

Various embodiments will now be described in more detail with reference to the figures. The systems and methods described herein provide one or more of the benefits mentioned above and/or various additional and/or alternative benefits that will be made apparent.

FIG. 1 illustrates an exemplary stereoscopic endoscope 100. Endoscope 100 may be manually controlled (e.g., by a surgeon performing a surgical procedure on a patient). Alternatively, endoscope 100 may be coupled to a computer-assisted surgical system and controlled using robotic technology. Endoscope 100 is representative of many different types of endoscopes within which the systems and methods described herein may be used. For example, the systems and methods described herein may alternatively be used with a monoscopic endoscope.

As shown, endoscope 100 includes a shaft 102 and a camera head 104 coupled to a proximal end of shaft 102. Camera head 104 is configured to be located external to the patient. Shaft 102 has a distal end that is configured to be inserted into surgical area of a patient. As used herein, a "surgical area" of a patient may, in certain examples, be entirely within the patient and may include an area within the patient near where a surgical procedure is planned to be performed, is being performed, or has been performed. In other examples, a surgical area may be at least partially external to the patient. In various implementations, shaft 102 is rigid (as shown in FIG. 1). Alternatively, shaft 102 may be jointed and/or flexible.

As shown, camera head 104 houses a right-side camera control unit 106-R, a left-side camera control unit 106-L, and an illuminator 108. Shaft 102 houses a right-side image sensor 110-R optically coupled to a right-side optic 112-R, a left-side image sensor 110-L optically coupled to a left-side optic 112-L, and an illumination channel 114. The right-side components (i.e., camera control unit 106-R, image sensor 110-R, and optic 112-R) implement a camera that captures images 116-R of the surgical area from a right-side perspective. Likewise, the left-side components (i.e., camera control unit 106-L, image sensor 110-L, and optic 112-L) implement a camera that captures images 116-L of the surgical area from a left-side perspective.

To capture images 116, illuminator 108 generates light, which is carried by one or more optical fibers in illumination channel 114 and output into the surgical area at a distal end of shaft 102. Optics 112, which may each be implemented by a lens or other suitable component, capture the light after the light reflects from patient anatomy and/or other objects within the surgical area.

The light captured by optics 112 is sensed by image sensors 110. Image sensors 110 may be implemented as any suitable image sensors such as charge coupled device ("CCD") image sensors, complementary metal-oxide semiconductor ("CMOS") image sensors, or the like. Image sensors 110-R and 110-L convert the sensed light into signals (e.g., video data) representative of images, and transmit the signals to camera control units 106 by way of conduits 118-R and 118-L, respectively. Conduits 118 may be any suitable communication link configured to handle high-speed transmission of data.

Camera control units 106 process the signals received from image sensors 110 and generate, based on the signals, data representative of images 116. Camera control units 106 then transmit the data to an external device (e.g., a computing device that displays the images and/or video formed by the images on a display screen). As shown, camera control units 106 are synchronously coupled to one another by way of a communicative link 120 so that images 116 are synchronized.

Additional or alternative components may be included in endoscope 100. For example, one or more or other optics not explicitly shown in FIG. 1 may be included in shaft 102 for focusing, diffusing, or otherwise treating light generated and/or sensed by endoscope 100. In some alternative examples, image sensors 110 can be positioned closer to the proximal end of shaft 102 or inside camera head 104, a configuration commonly referred to as a rod lens endoscope.

The systems and methods described herein may be implemented within endoscope 100. For example, the systems and methods described herein may be used to transmit data between electrically isolated electrical circuits within endoscope 100 (e.g., within camera head 104) at a data transmission rate that is greater than 1 Gbps.

Figure 2:
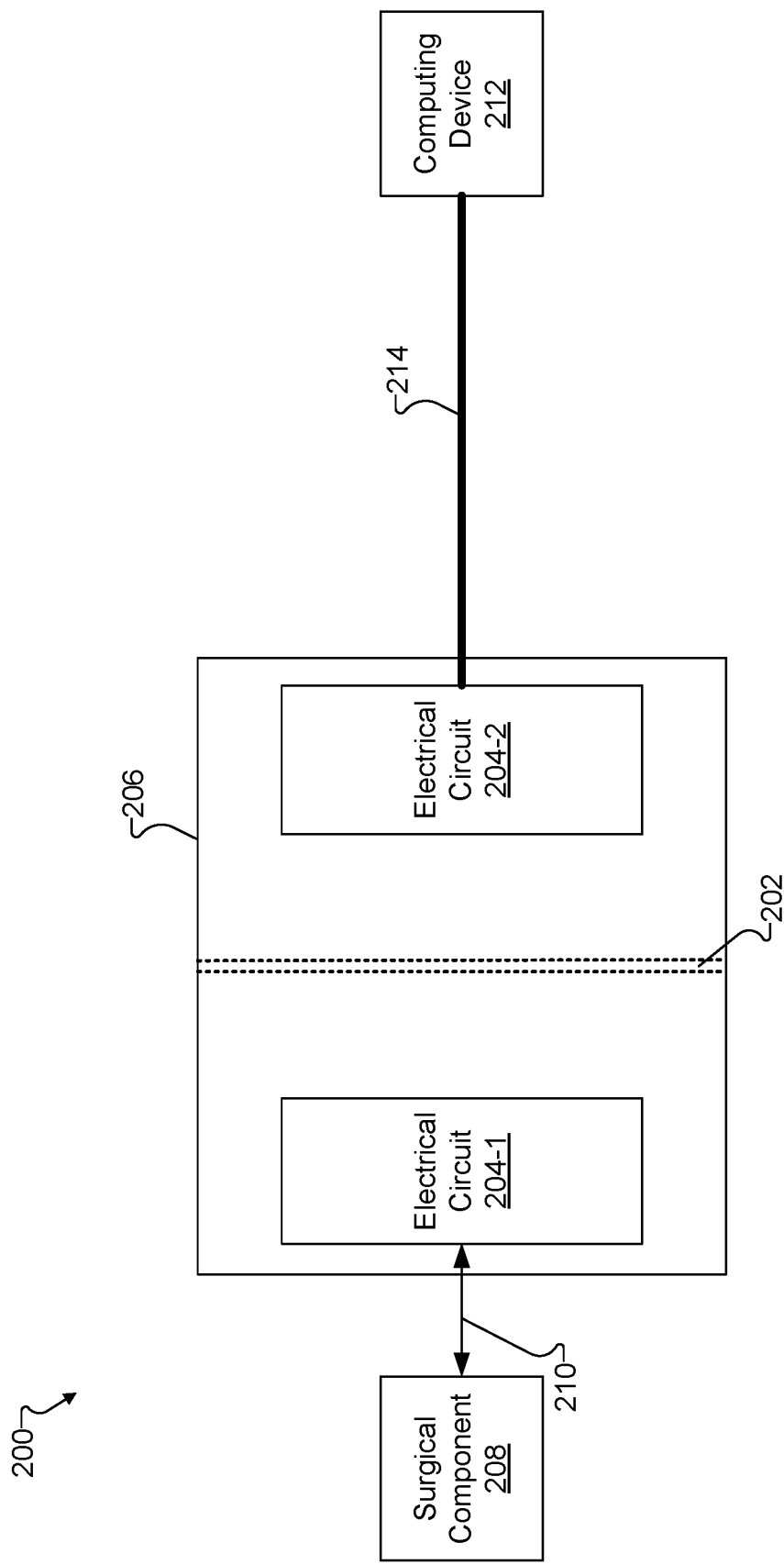
FIG. 2 illustrates an exemplary configuration in which an isolation barrier is used to electrically isolate a first electrical circuit on a PCB from a second electrical circuit on the PCB according to principles described herein.

FIG. 2 illustrates an exemplary configuration 200 in which an electrical isolation barrier 202 is used to electrically isolate a first electrical circuit 204-1 on a PCB 206 from a second electrical circuit 204-2 on PCB 206. As shown, first electrical circuit 204-1 is communicatively connected to a surgical component 208 by way of a connection 210, and second electrical circuit 204-2 is connected to a computing device 212 located off PCB 206 by way of an electrical cable 214. Each of these components will now be described.

PCB 206 is configured to mechanically support and electrically couple various electrical components included in electrical circuits 204-1 and 204-2 (collectively "electrical circuits 204"). For example, PCB 206 may include conductive pads to which electrical components may be soldered or otherwise electrically coupled, and conductive paths (e.g., traces, vias, etc.) that electrically interconnect the various electrical components. In some examples, non-conductive components (e.g., a housing of a free space optics interface assembly) may be attached (e.g., mechanically fastened, etc.) to PCB 206.

PCB 206 may be included within any suitable housing. For example, PCB 206 may be within a camera head (e.g., camera head 104) of an endoscope (e.g., endoscope 100). PCB 206 may alternatively be within any other type of surgical instrument and/or medical system component as may serve a particular implementation.

Electrical circuit 204-1 is configured to receive signals from surgical component 208 and generate or otherwise provide data based on the signals. The signals received from surgical component 208 may include data (e.g., video data) generated by image sensors 110 included in shaft 102. In other examples (e.g., when image sensors 110 are in camera housing 104), the signals received from surgical component 208 may be light signals provided by optics 112. Electrical circuit 204-1 may generate the data based on the signals in any suitable manner. For example, if the signals received from surgical component 208 include data generated by image sensors 110 included in shaft 102, electrical circuit 204-1 may generate data by processing the received data and generating new data based on the received data. In some alternative examples, electrical circuit 204-1 may simply receive and provide the data to electrical circuit 204-2 in its original format. If the signals received from surgical component 208 are light signals, electrical circuit 204-1 may generate the data by converting the light signals into data (e.g., video data) representative of images.

Electrical circuit 204-2 is configured to further process the data provided by electrical circuit 204-1 and/or transmit the data to computing device 212 by way of electrical cable 214. To this end, electrical circuits 204 may each include any number of passive or active electrical components (e.g., resistors, capacitors, integrated circuits ("ICs"), coils, etc.) interconnected in any suitable manner so as to perform one or more desired circuit operations. For example, electrical circuits 204 may include components that implement sensors 104, camera control units 112, and/or any other components included within camera head 104.

Electrical isolation barrier 202 electrically isolates electrical circuit 204-2 from electrical circuit 204-1. In other words, electrical isolation barrier 202 prevents any component included in electrical circuit 204-2 from being electrically connected in any way to any component included in electrical circuit 204-1. By so doing, electrical isolation barrier 202 prevents current (e.g., high frequency current applied to patient tissue by an electrosurgical tool) from being inadvertently capacitively coupled onto surgical component 208 when electrical cable 214 is in contact with a grounded surface (e.g., a floor of the operating room, a metal tray, etc.).

Electrical isolation barrier 202 may be implemented in any suitable manner. For example, electrical isolation barrier 202 may be implemented by PCB 206 including separate ground planes for each electrical circuit 204 (e.g., a first ground plane for electrical circuit 204-1 and a second ground plane separate and disconnected from the first ground plane for electrical circuit 204-2). Electrical isolation barrier 202 may be additionally or alternatively implemented in any other way (e.g., by maintaining a minimum physical distance between first and second electrical circuits 204, etc.).

Surgical component 208 may include any component configured to be positioned within a surgical area associated with a patient. In some examples, surgical component 208 may be a particular component of a surgical instrument used during a surgical procedure. For example, surgical component 208 may be implemented by a shaft (e.g., shaft 102) of an endoscope (e.g., endoscope 100). In some examples, surgical component 208 includes one or more conductive surfaces, such as an outer surface made out of a conductive metal, that may in some instances come in physical contact with patient tissue and/or patient fluid.

Surgical component 208 is connected to electrical circuit 204-1 by way of connection 210. Connection 210 may be implemented in any suitable manner. For example, one or more components within surgical component 208 may be electrically, optically, or otherwise coupled to electrical circuit 204-1. In this manner, electrical circuit 204-1 may receive signals from surgical component 208. To illustrate, if surgical component 208 is implemented by shaft 102 of endoscope 100, electrical circuit 204-1 may receive signals provided by one or more components in shaft 102. As another example, connection 210 may represent a capacitive coupling between surgical component 208 and electrical circuit 204-1. To illustrate, if surgical component 208 is a metal shaft of an endoscope, the metal shaft may be capacitively coupled to electrical circuit 204-1 by way of a capacitance that is created between the metal shaft and one or more conductive items (e.g., vias, traces, or components) included in electrical circuit 204-1.

Computing device 212 may include any suitable computing device located off PCB 206. For example, computing device 212 may be included in a computer-assisted surgical system, a display system, etc. Computing device 212 is configured to receive and process data transmitted from electrical circuit 204-2. For example, computing device 212 may display one or more images represented by the data on one or more display screens.

Electrical cable 214 includes one or more conductive wires configured to allow communication between second electrical circuit 204-2 and computing device 212. Electrical cable 214 further includes an insulative jacket that surrounds the one or more conductive wires. As mentioned, electrical cable 214 may come in contact with a grounded surface. When this happens, electrical cable 214 acts as a capacitor through which electrical current that has a sufficiently high frequency (e.g., greater than 100 kHz) can pass.

Figure 3:
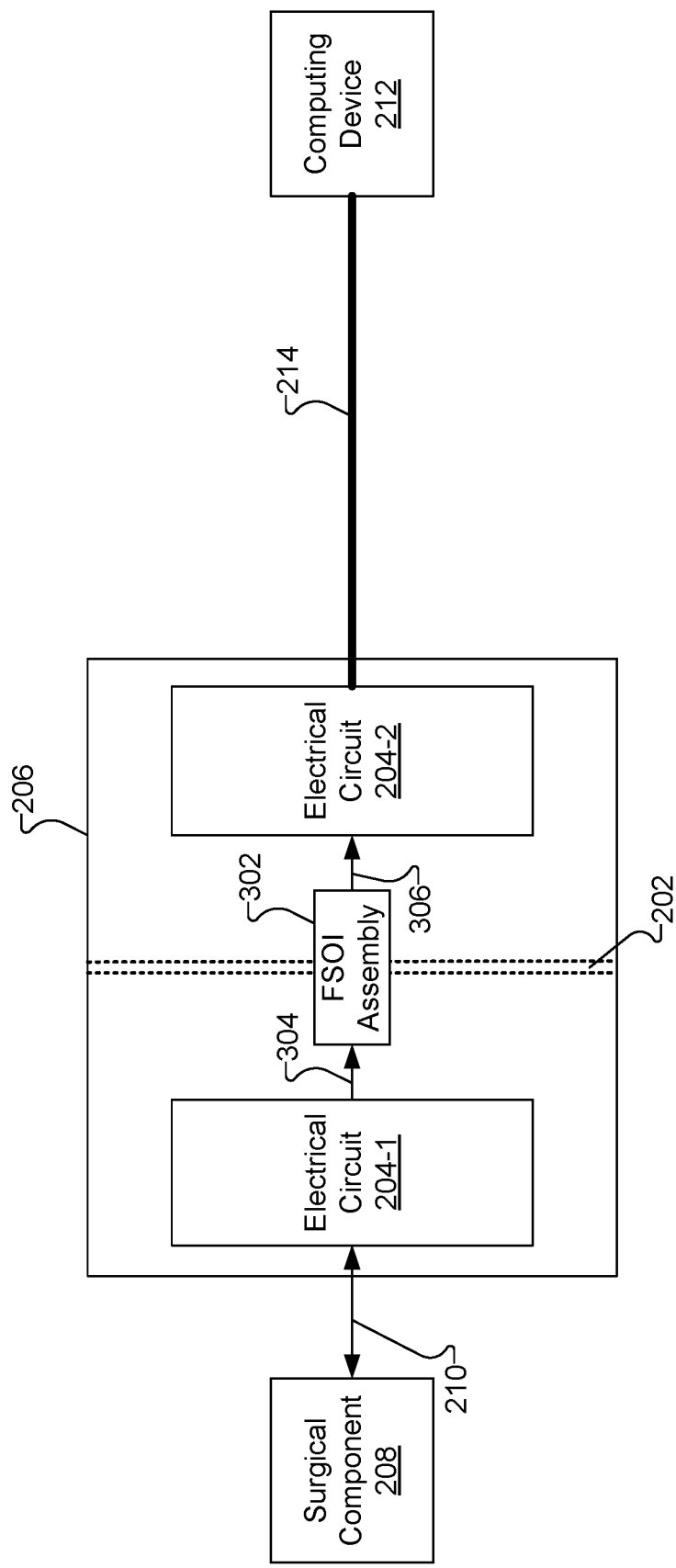
FIG. 3 illustrates an exemplary configuration in which a free space optics interface assembly is on a PCB to allow transmission of data between electrically isolated electrical circuits according to principles described herein.

FIG. 3 illustrates an exemplary configuration in which a free space optics interface ("FSOI") assembly 302 is on PCB 206 to allow transmission of data between first electrical circuit 204-1 and second electrical circuit 204-2. As shown, free space optics interface assembly 302 includes an input 304 that is electrically connected to first electrical circuit 204-1 and an output 306 that is electrically connected to second electrical circuit 204-2. Various components that are included in free space optics interface assembly 302 will now be described with reference to FIGS. 4-7.

Figure 4:
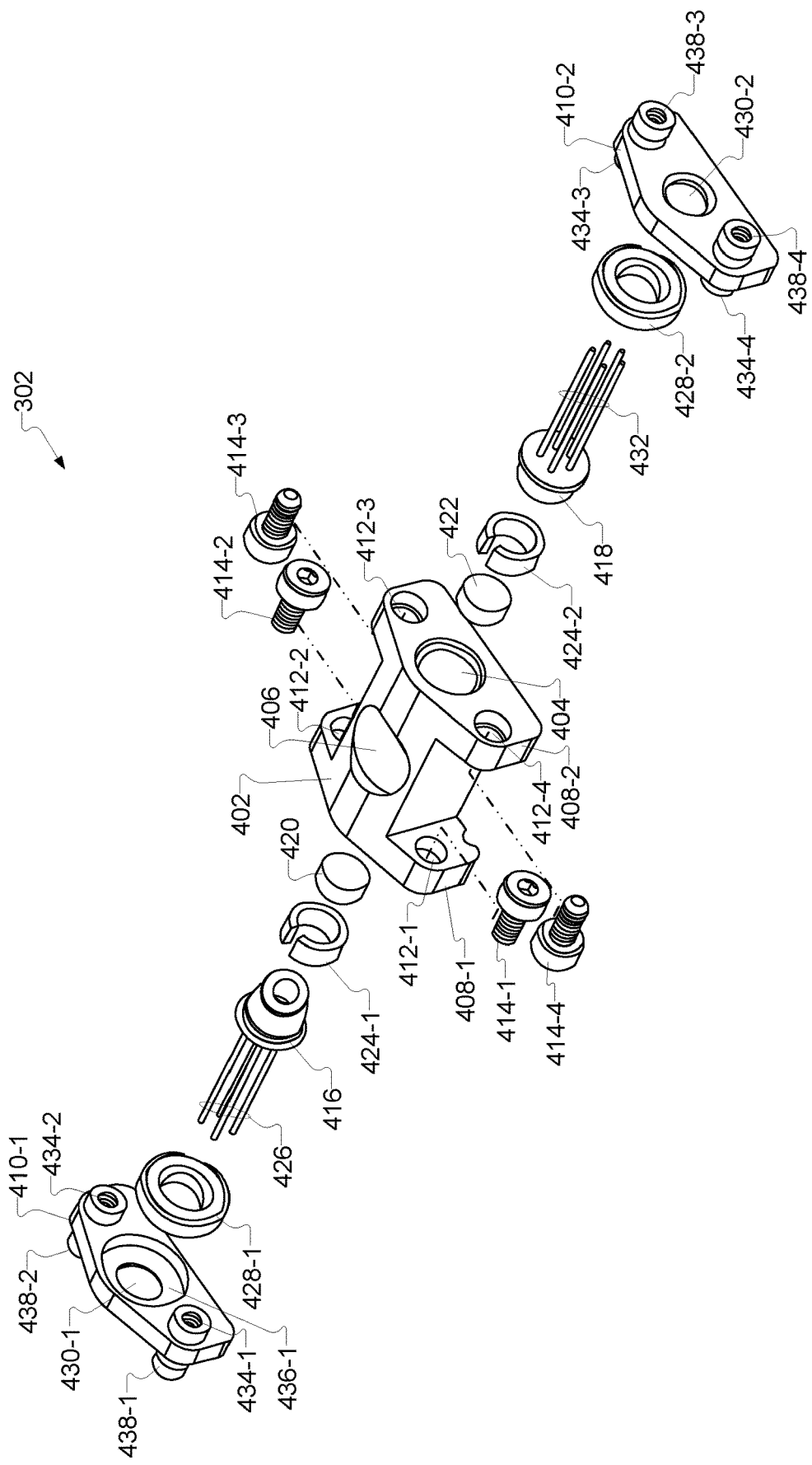
FIGS. 4-7 are various views of a free space optics interface assembly configured to be on a PCB according to principles described herein.

FIG. 4 shows an exploded view of free space optics interface assembly 302. As shown, free space optics interface assembly 302 includes a housing 402 that defines a free space chamber 404 in the housing 402. Free space chamber 404 is a hollow space within which various components are located. In the examples provided herein, free space chamber 404 is cylindrically shaped. However, free space chamber 404 may be alternatively shaped as may serve a particular implementation.

Housing 402 may be made out of any suitable material. For example, housing 402 may be made out of a non-conductive material (e.g., a polyether ether ketone ("PEEK") material) configured to provide electrical isolation and withstand an operating room sterilization process.

As shown, a top surface of housing 402 includes a cutout 406 configured to allow placement of free space optics interface assembly 302 onto PCB 206. For example, cutout 406 may receive a pick and place tool (e.g., a suction cup), which may be used to place free space optics interface assembly 302 onto PCB 206.

As shown, housing 402 further includes end flanges 408-1 and 408-2 (collectively "end flanges 408"). End flanges 408 allow fastening of end plates 410 (e.g., end plates 410-1 and 410-2) to housing 402, which hermetically seals various components within free space chamber 404, as will be described below. To this end, end flanges 408 includes a plurality of holes 412 (e.g., holes 412-1 through 412-4) through which fastening screws 414 (e.g., screws 414-1 through 414-4) may pass.

FIG. 4 shows various components configured to be positioned in free space chamber 404. For example, an optical transmitter 416, an optical receiver 418, a collimating lens 420, a focusing lens 422, and split rings 424 (e.g., split rings 424-1 and 424-2) are configured to be positioned in free space chamber 404.

Optical transmitter 416 may be positioned at a first end of free space chamber 404 and includes input pins 426 (or any other input) configured to be electrically coupled to first electrical circuit 204-1. To this end, input pins 426 are configured to extend through an opening of an O-ring 428-1 (described below) and through an opening 430-1 of end plate 410-1. Optical transmitter 416 includes any suitable transmitter diode (e.g., a vertical-cavity surface-emitting laser ("VCSEL")) configured to transmit modulated light representative of data (e.g., data provided by electrical circuit 104-1) into free space chamber 404. Moreover, even though optical transmitter 416 is shown in FIG. 4 as having four input pins 426, it will be recognized that optical transmitter 416 may alternatively include any other number of input pins 426 as may serve a particular implementation.

Optical receiver 418 may be positioned at a second end of free space chamber 404 opposite the first end and includes output pins 432 (or any other output) configured to be electrically coupled to second electrical circuit 204-2. To this end, output pins 432 are configured to extend through an opening of an O-ring 428-2 (described below) and through an opening 430-2 of end plate 410-2. Optical receiver 418 includes any suitable receiver diode configured to receive modulated light transmitted by optical transmitter 416. Moreover, even though optical receiver 418 is shown in FIG. 4 as having five output pins 432, it will be recognized that optical receiver 418 may alternatively include any other number of output pins 432 as may serve a particular implementation.

Collimating lens 420 and focusing lens 422 may both be positioned in free space chamber 404 between optical transmitter 416 and optical receiver 418. Collimating lens 420 is configured to collimate light transmitted by optical transmitter 416. Focusing lens 422 is configured to focus the collimated light so that the light can be received by optical receiver 418. It will be recognized that in some alternative examples, free space optics interface assembly 302 does not include any lenses in free space chamber 404.

Split rings 424 are configured to secure lenses 420 and 422 in free space chamber 404. For example, split ring 424-1 may be positioned in free space chamber 404 in between optical transmitter 416 and collimating lens 420 to secure collimating lens 420 in free space chamber 404. Likewise, split ring 424-2 may be positioned in free space chamber 404 in between optical receiver 418 and focusing lens 422 to secure focusing lens 422 in free space chamber 404. Each split ring 424 has an outer diameter that is slightly larger than the inner diameter of free space chamber 404 such that each split ring 424 is slightly compressed to fit in free space chamber 404. In this manner, split rings 424 provide positive retention of lenses 420 and 422 against retention stops (not shown in FIG. 4) in free space chamber 404. Split rings 424 may be made out of any suitable non-conductive material (e.g., PEEK) and advantageously secure lenses 420 and 422 in free space chamber 404 without the use of adhesives. By not using any adhesives to secure lenses 420 and 422 (or any other component) in free space chamber 404, the systems and methods described herein obviate the need for testing to ensure that no outgassing or other decomposition of adhesives occurs during an autoclave or other sterilization process.

End plates 410 and O-rings 428 are configured to hermetically seal optical transmitter 416, optical receiver 418, lenses 420 and 422, and split rings 424 in free space chamber 404. For example, end plates 410 include threaded receptacles 434 (e.g., receptacles 434-1 through 434-4) configured to receive screws 414 in order to physically secure end plates 410 to end flanges 408 of housing 402. Each O-ring 428 is configured to fit within a cavity (e.g., cavity 436-1) of its corresponding end plate 410 such that when end plates 410 are secured to end flanges 408 of housing 402, O-rings 428 compress against end flanges 408 in a manner that hermetically seals optical transmitter 416, optical receiver 418, lenses 420 and 422, and split rings 424 in free space chamber 404. End plates 410 and O-rings 428 may be made out of any suitable material configured to provide the hermetic sealing of components in free space chamber 404. For example, end plates 410 may be made out of stainless steel, and O-rings 428 may be made out of any heat-resistant elastic material (e.g., rubber, an elastomer, PTFE, silicone, a perfluoroelastomer material, etc.). In some examples, as will be illustrated below, O-rings 428 are implemented by X-section O-rings (i.e., O-rings that have an X-shaped cross-section). X-section O-rings may provide greater stability and reliability compared to conventional O-rings.

In some examples, as will be described below, end plates 410 are also physically secured to feedthrough assemblies that provide electrical coupling of optical transmitter 416 and optical receiver 418 to first and second electrical circuits 204-1 and 204-2, respectively. To this end, threaded receptacles 438 (e.g., receptacles 438-1 through 438-4) are on an outer surface of end plates 410. End plates 410 may alternatively be secured to feedthrough assemblies in any other manner.

Figure 5:
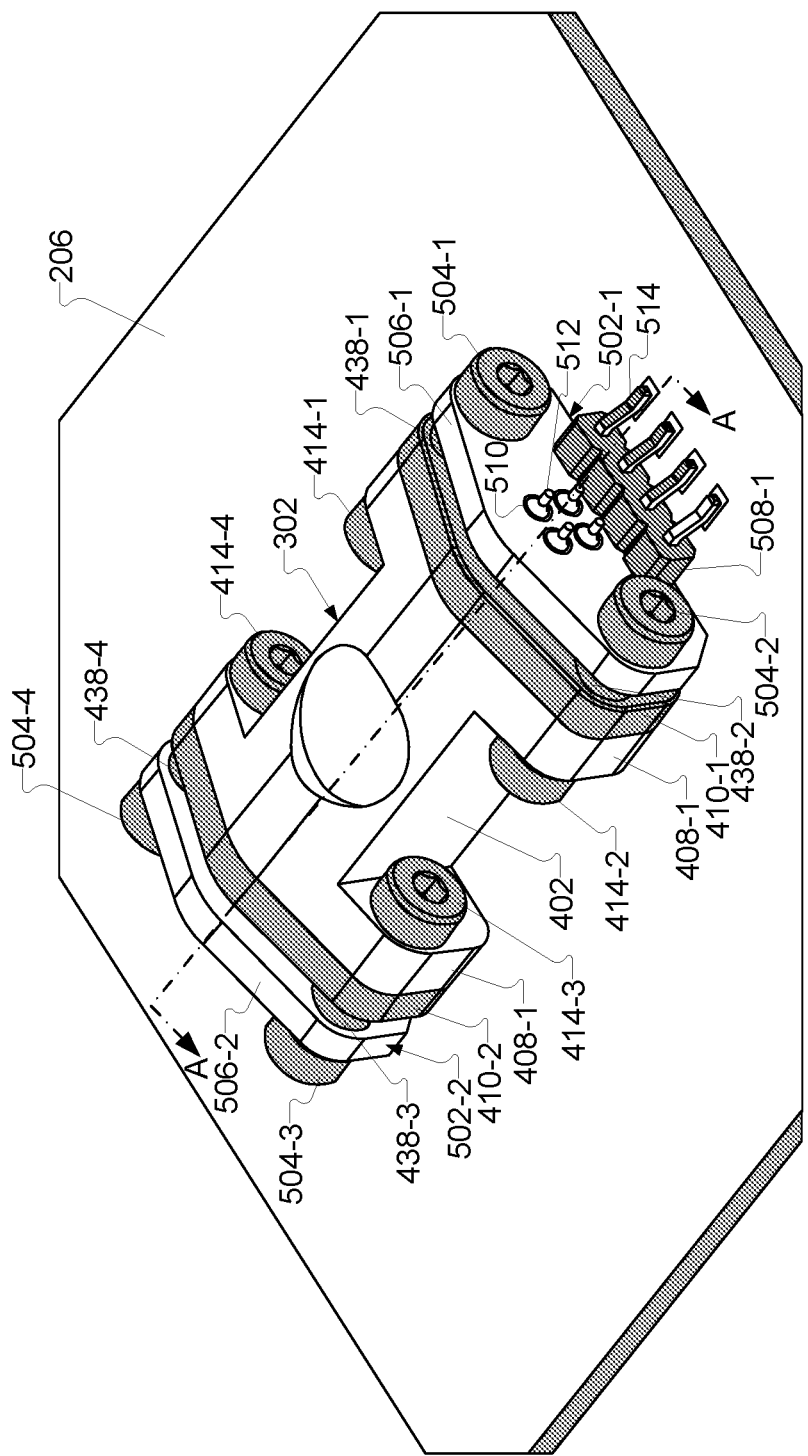

FIG. 5 shows a perspective view of an assembled free space optics interface assembly 302 on PCB 206. In the example of FIG. 5, the view of free space optics interface assembly 302 has been rotated with respect to the view shown in FIG. 4 such that the transmitter side of free space optics interface assembly 302 is shown as being towards the bottom of the page.

Figure 6A:
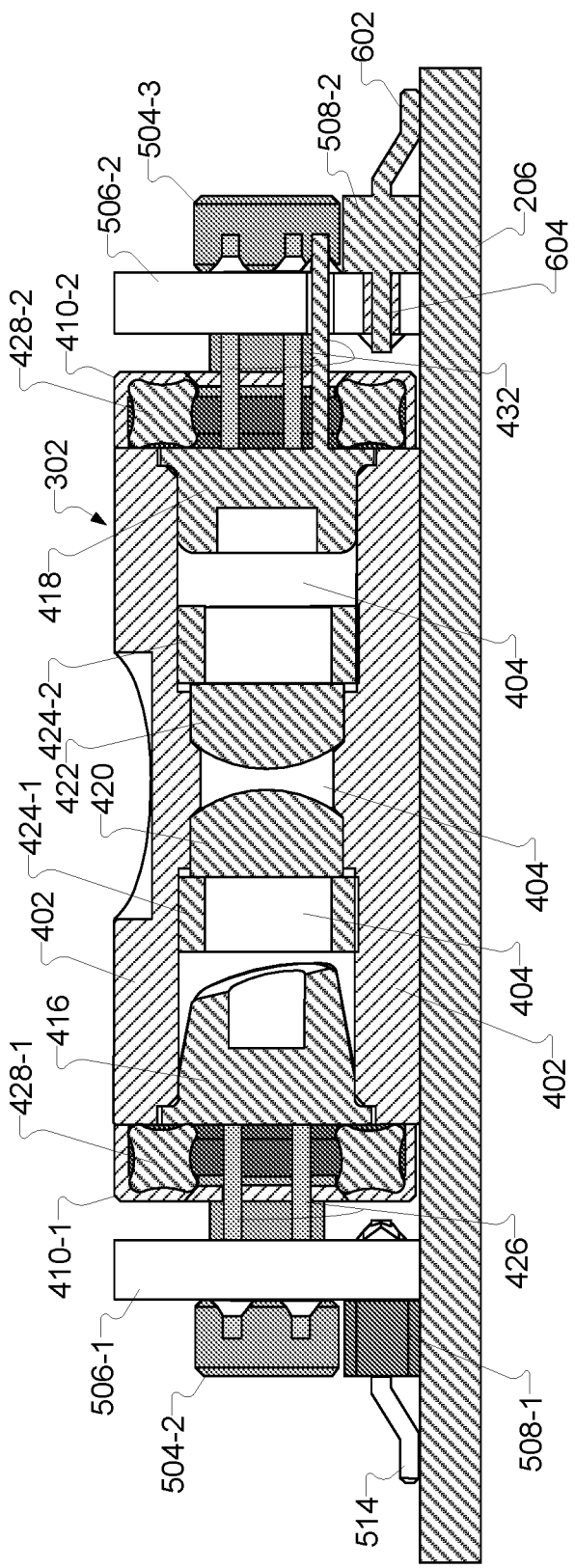
Figure 6B:
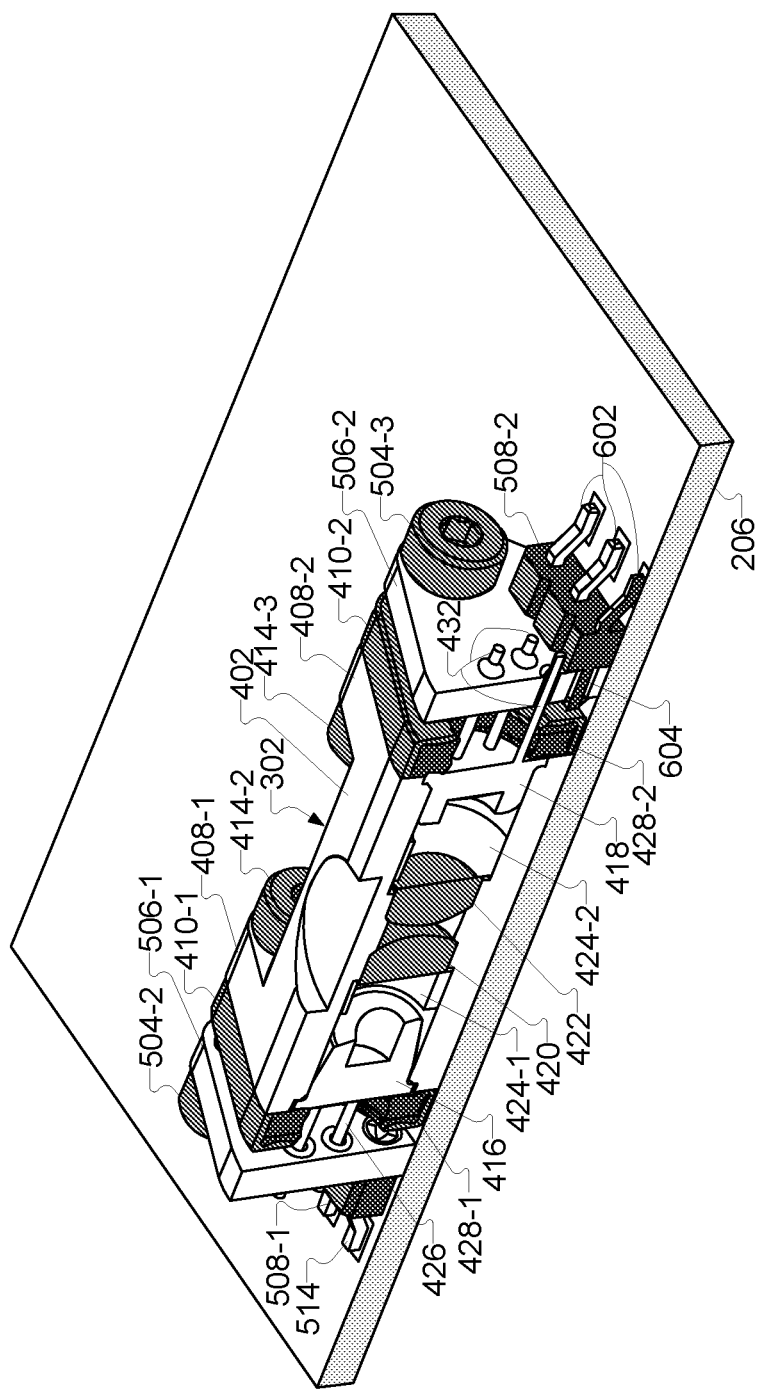

As shown, end plates 410 are secured to end flanges 418 of housing 402 using screws 414. Components internal to housing 402 of assembled free space optics interface assembly 302 are not shown in FIG. 5, but are shown in FIGS. 6A and 6B, as will be described below.

As shown in FIG. 5, end plate 410-1 is secured to a first feedthrough assembly 502-1 and end plate 410-2 is secured to a second feedthrough assembly 502-2. This may be performed in any suitable manner. For example, as shown, screws 504-1 and 504-2 are inserted through holes included in feedthrough assembly 502-1 and into receptacles 438-1 and 438-2 of end plate 410-1. Likewise, screws 504-3 and 504-4 are inserted through holes included in feedthrough assembly 502-2 and into receptacles 438-3 and 438-4 of end plate 410-2.

Feedthrough assembly 502-1 provides electrical connection of input pins 426 (or any other input) of optical transmitter 416 to first electrical circuit 204-1. Likewise, feedthrough assembly 502-2 provides electrical connection of output pins 432 (or any other output) of optical receiver 418 to second electrical circuit 204-2. To this end, feedthrough assemblies 502-1 and 502-2 (collectively "feedthrough assemblies 502") each include a tombstone PCB and a surface mount technology ("SMT") pin adapter. For example, as shown in FIG. 5, feedthrough assembly 502-1 includes a tombstone PCB 506-1 and an SMT pin adapter 508-1. Feedthrough assembly 502-2 likewise includes a tombstone PCB 506-2 and an SMT pin adapter 508-2, although SMT pin adapter 508-2 is not shown in the perspective view of FIG. 5 (it will be shown in subsequent figures). Tombstone PCBs 506-1 and 506-2 are collectively referred to as "tombstone PCBs 506", and SMT pin adapters 508-1 and 508-2 are collectively referred to as "SMT pin adapters 508".

As shown, each tombstone PCB 506 is on and perpendicular to PCB 206. Each tombstone PCB 506 includes a plurality of conductive receptacles (e.g., receptacle 510, which is a part of tombstone PCB 506-1) configured to receive and be soldered to a plurality of conductive pins (e.g., pin 512) that are either a part of optical transmitter 416 or optical receiver 418. For example, FIG. 5 shows that receptacle 510 is soldered to pin 512, which may implement one of pins 426 of optical transmitter 416. Each tombstone PCB 506 also includes a plurality of conductive pads (not shown) electrically coupled to the tombstone PCB's conductive receptacles by way of a plurality of conductive paths (e.g., traces, vias, etc.). Other components (e.g., decoupling capacitors, etc.) may optionally be on tombstone PCBs 506 as may serve a particular implementation.

Each SMT pin adapter 508 includes a plurality of conductive pins (e.g., pin 514, which is a part of SMT pin adapter 508-1). The conductive pins that are included as part of each SMT pin adapter 508 are electrically coupled (e.g., soldered) to first or second electrical circuit 204-1 or 204-2. For example, pin 514 is electrically coupled to first electrical circuit 204-1. The conductive pins are also electrically coupled (e.g., by way of conductive feedthroughs internal to SMT pin adapters 508, as illustrated below) to the conductive pads included on tombstone PCBs 506. In this manner, electrical circuits 204-1 and 204-2 are electrically coupled to optical transmitter 416 and optical receiver 418, respectively.

It will be recognized that in some alternative examples, feedthrough assemblies 502 are not included in the systems and methods described herein. In these alternative embodiments, input pins 426 of optical transmitter 416 and output pins 432 of optical receiver 418 may be bent (e.g., at a ninety degree angle as they exit end plates 410) and electrically coupled (e.g., soldered) directly to PCB 206.

FIGS. 6A-6B show cross-sectional views of free space optics interface assembly 302 and tombstone PCBs 506 taken along line A-A shown in FIG. 5. Various features distinctly shown in the cross-sectional views of FIGS. 6A-6B (and, in some cases, not explicitly shown in the views of FIGS. 4-5) will now be described.

As shown in FIGS. 6A-6B, optical transmitter 416, optical receiver 418, collimating lens 420, focusing lens 422, and split rings 424 are all in free space chamber 404 defined by housing 402. In this configuration, modulated light transmitted by optical transmitter 416 is collimated by collimating lens 420, focused by focusing lens 422, and then received by optical receiver 418.

FIGS. 6A-6B also show that O-rings 428 may be implemented as X-section O-rings. As described above, X-section O-rings are configured to hermetically seal optical transmitter 416, optical receiver 418, collimating lens 420, focusing lens 422, and split rings 424 in free space chamber 404 defined by housing 402.

FIGS. 6A-6B also show that SMT pin adapter 508-2 includes conductive pins 602 (not shown in FIG. 5 due to the viewing angle of FIG. 5) soldered to PCB 206. A feedthrough 604 of SMT pin adapter 508-2 is shown in FIGS. 6A-6B, which is configured to conductively couple feedthrough pin 602 to one of the output pins 432 of optical receiver 418.

Figure 7:
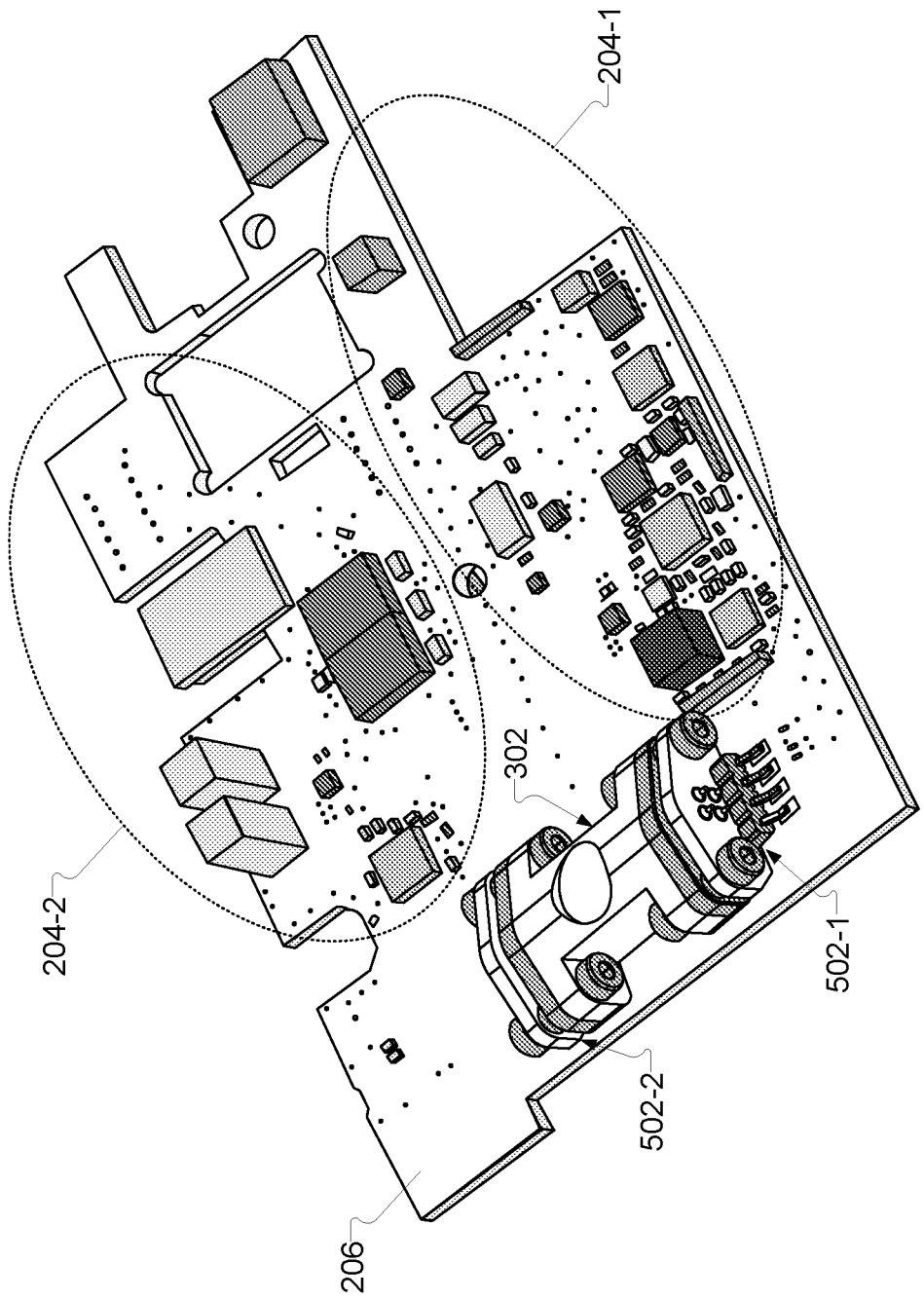

FIG. 7 shows an exemplary perspective view in which free space optics interface assembly 302 is on PCB 206 together with various components included within first electrical circuit 204-1 and second electrical circuit 204-2. PCB 206 shown in FIG. 7 may be included, for example, within a surgical instrument (e.g., camera head 104 of endoscope 100).

Optical transmitter 416 (not shown in FIG. 7) is electrically coupled to one or more components within first electrical circuit 204-1 by way of feedthrough assembly 502-1. For example, optical transmitter 416 may be electrically coupled to a modulator component included in first electrical circuit 204-1. The modulator component may be configured to direct optical transmitter 416 to transmit modulated light representative of data into free space chamber 404 defined by housing 402 of free space optics interface assembly 302.

Likewise, optical receiver 418 (not shown in FIG. 7) is electrically coupled to one or more components within second electrical circuit 204-2 by way of feedthrough assembly 502-2. For example, optical receiver 418 may be electrically coupled to a demodulator component included in second electrical circuit 204-2. The demodulator component may be configured to demodulate modulated light received by optical receiver 418 back into data.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A medical system comprising:
a first electrical circuit on a printed circuit board ("PCB");
a second electrical circuit on the PCB and electrically isolated from the first electrical circuit;
a free space optics interface assembly on the PCB, the free space optics assembly comprising
a housing defining a free space chamber in the housing,
an optical transmitter having an input that is electrically coupled to the first electrical circuit, and
an optical receiver having an output that is electrically coupled to the second electrical circuit;
a feedthrough assembly electrically connecting the input of the optical transmitter to the first electrical circuit, the feedthrough assembly comprising a tombstone PCB on and perpendicular to the PCB upon which the first and second electrical circuits are located, the tombstone PCB comprising
a first conductive receptacle that receives and is soldered to a first input pin of the optical transmitter,
a second conductive receptacle that receives and is soldered to a second input pin of the optical transmitter,
a first conductive pad electrically coupled to the first conductive receptacle by way of a first conductive path, and
a second conductive pad electrically coupled to the second conductive receptacle by way of a second conductive path; and
a surface mount technology pin adapter electrically coupled to the first and second conductive pads and comprising a plurality of conductive pins soldered to the PCB such that the first and second input pins of the optical transmitter are electrically connected to the first electrical circuit.

2. The medical system of claim 1, wherein:
the optical transmitter is at a first end of the free space chamber and configured to optically transmit, into the free space chamber, modulated light representative of data provided by the first electrical circuit; and
the optical receiver is at a second end of the free space chamber opposite the first end and is configured to receive the modulated light transmitted by the optical transmitter into the free space chamber.

3. The medical system of claim 2, wherein the first electrical circuit comprises a modulator component electrically coupled to the input of the optical transmitter, the modulator component configured to direct the optical transmitter to transmit the modulated light into the free space chamber.

4. The medical system of claim 2, wherein the second electrical circuit comprises a demodulator component electrically coupled to the output of the optical receiver, the demodulator component configured to demodulate the modulated light back into the data.

5. The medical system of claim 2, wherein the free space optics assembly further comprises:
a collimating lens in the free space chamber between the optical transmitter and the optical receiver; and
a focusing lens in the free space chamber between the optical transmitter and the optical receiver;
wherein
the collimating lens is configured to collimate the modulated light transmitted by the optical transmitter, and
the focusing lens is configured to focus the collimated modulated light onto the optical receiver.

6. The medical system of claim 5, wherein the free space optics assembly further comprises:
a first split ring in the free space chamber between the optical transmitter and the collimating lens, the first split ring configured to secure the collimating lens in the free space chamber; and
a second split ring in the free space chamber between the optical receiver and the focusing lens, the second split ring configured to secure the focusing lens in the free space chamber.

7. The medical system of claim 1, wherein the free space optics interface assembly further comprises:
a first end plate secured to a first end flange of the housing and having a first opening through which pins of the optical transmitter extend;
a second end plate secured to a second end flange of the housing and having a second opening through which pins of the optical receiver extend;
a first O-ring in the first end plate and located to compress against the first end flange of the housing when the first end plate is secured to the first end flange of the housing; and
a second O-ring within the second end plate and located to compress against the second end flange of the housing when the second end plate is secured to the second end flange of the housing;
wherein the first and second O-rings hermetically seal the optical transmitter and the optical receiver within the housing.

8. The medical system of claim 7, wherein the first and second O-rings comprise X-section O-rings.

9. The medical system of claim 1, wherein the optical transmitter comprises a vertical-cavity surface-emitting laser.

10. The medical system of claim 1, wherein the first electrical circuit is configured to transmit data to the second electrical circuit by way of the free space optics interface assembly at a data transmission rate of greater than 1 gigabit per second.

11. The medical system of claim 10, wherein the second electrical circuit is configured to transmit, by way of an electrical cable, the data to a computing device located off the PCB.

12. The medical system of claim 10, wherein the first electrical circuit is configured to:
receive signals received from a surgical component configured to be positioned within a surgical area of a patient; and
generate the data based on the signals.

13. The medical system of claim 12, wherein:
the PCB is in a camera head of an endoscope; and
the surgical component comprises a shaft that extends from the camera head and that comprises a distal end configured to be positioned within the surgical area.

14. The medical system of claim 12, wherein the electrical isolation of the second electrical circuit from the first electrical circuit is configured to prevent electrical current from being capacitively coupled onto the surgical component.

15. The medical system of claim 1, wherein the PCB comprises:
a first ground plane for the first electrical circuit; and
a second ground plane for the second electrical circuit, the second ground plane separate from the first ground plane;
wherein the first and second ground planes electrically isolate the second electrical circuit from the first electrical circuit.

16. A medical system comprising:
a first electrical circuit on a printed circuit board ("PCB") and configured to provide data;
a second electrical circuit on the PCB and electrically isolated from the first electrical circuit; and
a free space optics interface assembly on the PCB, the free space optics assembly comprising
a housing defining a free space chamber in the housing,
an optical transmitter in the housing at a first end of the free space chamber, the optical transmitter having input pins that are electrically coupled to the first electrical circuit by way of a first feedthrough assembly and configured to optically transmit modulated light representative of the data into the free space chamber,
an optical receiver in the housing at a second end of the free space chamber opposite the first end, the optical receiver having output pins that are electrically coupled to the second electrical circuit and configured to receive the modulated light transmitted into the free space chamber,
a first end plate secured to a first end flange of the housing and having a first opening through which the input pins of the optical transmitter extend,
a second end plate secured to a second end flange of the housing and having a second opening through which the output pins of the optical receiver extend,
a first O-ring in the first end plate and located to compress against the first end flange of the housing when the first end plate is secured to the first end flange of the housing, and
a second O-ring in the second end plate and configured to compress against the second end flange of the housing when the second end plate is secured to the second end flange of the housing;
wherein the first and second O-rings hermetically seal the optical transmitter and the optical receiver within the housing.

17. The medical system of claim 16, wherein the free space optics assembly further comprises:
a collimating lens in the free space chamber between the optical transmitter and the optical receiver; and
a focusing lens in the free space chamber between the optical transmitter and the optical receiver;
wherein
the collimating lens is configured to collimate the modulated light transmitted by the optical transmitter, and
the focusing lens is configured to focus the collimated modulated light onto the optical receiver.

18. An endoscope comprising:
a camera head; and
a shaft that extends from the camera head and that comprises
  a distal end configured to be positioned within a surgical area of a patient, and
  one or more components within the shaft that are configured to provide signals to the camera head;
wherein the camera head houses
  a printed circuit board ("PCB"),
  a first electrical circuit on the PCB and configured to receive the signals, and
    generate data based on the signals,
  a second electrical circuit on the PCB and electrically isolated from the first electrical circuit, and
  a free space optics interface assembly on the PCB, the free space optics assembly comprising
    a housing defining a free space chamber in the housing,
    an optical transmitter having an input that is electrically coupled to the first electrical circuit, and
    an optical receiver having an output that is electrically coupled to the second electrical circuit;
  a feedthrough assembly electrically connecting the input of the optical transmitter to the first electrical circuit, the feedthrough assembly comprising a tombstone PCB on and perpendicular to the PCB upon which the first and second electrical circuits are located, the tombstone PCB comprising
    a first conductive receptacle that receives and is soldered to a first input pin of the optical transmitter,
    a second conductive receptacle that receives and is soldered to a second input pin of the optical transmitter,
    a first conductive pad electrically coupled to the first conductive receptacle by way of a first conductive path, and
    a second conductive pad electrically coupled to the second conductive receptacle by way of a second conductive path; and
  a surface mount technology pin adapter electrically coupled to the first and second conductive pads and comprising a plurality of conductive pins soldered to the PCB such that the first and second input pins of the optical transmitter are electrically connected to the first electrical circuit.

19. The endoscope of claim 18, wherein:
the optical transmitter is at a first end of the free space chamber and configured to optically transmit modulated light representative of the data into the free space chamber; and
the optical receiver is at a second end of the free space chamber opposite the first end and is configured to receive the modulated light transmitted by the optical transmitter into the free space chamber.

* * * * *